(12) United States Patent
Shyue et al.

(10) Patent No.: US 11,097,134 B2
(45) Date of Patent: Aug. 24, 2021

(54) CAVEOLIN-1 ANTIBODY FOR USE IN TREATING BRAIN INFLAMMATION AND INJURY AND IMPROVING FUNCTIONAL RECOVERY

(71) Applicant: Academia Sinica, Taipei (TW)

(72) Inventors: Song-Kun Shyue, Taipei (TW); Szu-Fu Chen, Taipei (TW); Chun-Hu Wu, Taipei (TW); Che-Feng Chang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/874,019

(22) Filed: May 14, 2020

(65) Prior Publication Data

US 2020/0362030 A1    Nov. 19, 2020

Related U.S. Application Data

(60) Provisional application No. 62/848,863, filed on May 16, 2019.

(51) Int. Cl.
*A61P 25/00* (2006.01)
*C07K 16/28* (2006.01)
*A61K 39/00* (2006.01)

(52) U.S. Cl.
CPC .............. *A61P 25/00* (2018.01); *C07K 16/28* (2013.01); *A61K 2039/505* (2013.01); *A61K 2039/54* (2013.01)

(58) Field of Classification Search
None
See application file for complete search history.

(56) References Cited

U.S. PATENT DOCUMENTS

| | | | | |
|---|---|---|---|---|
| 2001/0012890 A1* | 8/2001 | Thompson | ......... | C12N 15/1138 536/24.1 |
| 2010/0266540 A1* | 10/2010 | Craven | ........... | A61K 45/06 424/85.4 |
| 2013/0183706 A1* | 7/2013 | Lacasa | ........... | C12N 5/0653 435/29 |
| 2015/0045247 A1* | 2/2015 | Pottier | ........... | A61P 17/02 506/9 |
| 2016/0176961 A1* | 6/2016 | Baker | ........... | A61P 9/10 424/139.1 |
| 2017/0348393 A1* | 12/2017 | Schwartz-Eisenbach | ........... | A61K 38/215 |
| 2018/0030535 A1* | 2/2018 | Bang | ........... | G01N 33/6893 |

OTHER PUBLICATIONS

SCBT "caveolin-1 antibody n-20: sc-894" accessed from scbt.com on Oct. 7, 2020 (Year: 2020).*
Li "Electroacupuncture Exerts Neuroprotection through Caveolin-1 Mediated Molecular Pathway in Intracerebral Hemorrhage of Rats" neural plasticity (Year: 2016).*
Hiromura "Caveolin-1, a binding protein of CD26, is essential for the antiinflammatory effects of dipeptidyl peptidase-4 inhibitors on human and mouse macrophages" Biochemical and Biophysical Research Communications 495 (2018) 223e229 (Year: 2018).*
Kuo "Anti-caveolin-1 Antibodies as Anti-Prostate Cancer Therapeutics" Hybridoma vol. 31, No. 2, (Year: 2012).*
Cook "Intracerebroventricular administration of drugs" Pharmacotherapy. Jul. 2009;29(7):832-45 (abstract only) (Year: 2009).*
Liu "Focused Ultrasound Enhances Central Nervous System Delivery of Bevacizumab for Malignant Glioma Treatment" Radiology: vol. 281: No. 1 (Year: 2016).*
Weber "Characterization of the Blood Brain Barrier Disruption in the Photothrombotic Stroke Model" Frontiers in Physiology 11 (Year: 2020).*
Chang CF, Chen SF, Lee TS, Lee HF, Chen SF, Shyue SK: Caveolin-1 deletion reduces early brain injury after experimental intracerebral hemorrhage. Am J Pathol 2011, 176:1749-1761.

* cited by examiner

*Primary Examiner* — Adam Weidner
(74) *Attorney, Agent, or Firm* — Hsiu-Ming Saunders; Intellectual Property Connections Inc.

(57) ABSTRACT

A method for treating a neurological disorder, symptom or disease that is associated with an increase in the brain levels of caveolin-1 (Cav-1) in a subject in need thereof is disclosed. The method comprises administering to the subject in need thereof a composition comprising: (a) a therapeutically effective amount of an antibody specific against the Cav-1 or an antigen-binding fragment thereof; and (b) a pharmaceutically acceptable carrier. Methods for reducing cerebral inflammation, brain tissue damage, brain neuronal death, and improving behavioral outcomes or functional recovery related to a hemorrhagic stroke in a subject in need thereof are also disclosed.

14 Claims, 9 Drawing Sheets

CAVEOLIN-1 ANTIBODY FOR USE IN TREATING BRAIN INFLAMMATION AND INJURY AND IMPROVING FUNCTIONAL RECOVERY

REFERENCE TO RELATED APPLICATION

The present application claims the priority to U.S. Provisional Application Ser. No. 62/848,863, May 16, 2019, which is herein incorporated by reference in its entirety.

FIELD OF THE INVENTION

The present invention relates generally to Caveolin-1 antibodies and methods for treating Caveolin-1-associated disease.

BACKGROUND OF THE INVENTION

Intracerebral hemorrhage (ICH) is a type of stroke caused by bleeding within the brain tissue or ventricles. ICH accounts for 10% to 15% of all stroke but results in high rates of mortality and morbidity. In ICH, the components released from serum and blood cells cause neuronal cell damage and trigger strong inflammatory response which lead to the infiltration of circulating immune cells and release of inflammatory mediators resulting in the breakdown of blood-brain barrier, secondary neuronal damage and brain edema formation. A number of therapeutic approaches have been tested clinically, effective treatment however remains unsatisfactory.

Accordingly, there is a need in the art for providing an effective approach for reducing brain injury caused by ICH.

SUMMARY OF THE INVENTION

The invention relates to use of an antibody specific against caveolin-1 (Cav-1) or an antigen-binding fragment thereof in the manufacture of a medicament for: (1) treating a neurological disorder, symptom or disease that is associated with an increase in the brain levels of caveolin-1 (Cav-1) in a subject in need thereof; (2) reducing cerebral inflammation, brain tissue damage, brain neuronal death, and improving behavioral outcomes or functional recovery related to a hemorrhagic stroke in a subject in need thereof; or (3) treating a hemorrhagic stroke in a subject in need thereof.

In one embodiment, the subject in need thereof is at risk of having the occurrence of the neurological disorder, symptom or disease within 1 hour or within 2 hours.

In another embodiment, the subject in need thereof is within 6 hours of the occurrence of the neurological disorder, symptom or disease. That is, the subject in need thereof is within 6 hours before or after the occurrence of the neurological disorder, symptom or disease. That is, the subject in need thereof is within 0.5, 1, 2, 3, 4, 5, or 6 hours after or before the occurrence of the neurological disorder, symptom or disease.

The subject in need thereof is within 1-24 hours or within 3-24 hours window of the occurrence of the hemorrhagic stroke. That is, the subject in need thereof is within 1-24 hours or within 3-24 hours after or before the occurrence of the hemorrhagic stroke.

In one aspect, the invention relates to a method for treating a neurological disorder, symptom or disease that is associated with an increase in the brain levels of caveolin-1 (Cav-1) in a subject in need thereof. The method comprises administering to the subject in need thereof a composition comprising:
(a) a therapeutically effective amount of an antibody specific against the Cav-1 or an antigen-binding fragment thereof; and
(b) a pharmaceutically acceptable carrier,
to treat the neurological disorder, symptom or disease that is associated with the increase in the brain levels of the Cav-1 in the subject in need thereof.

In one embodiment, the neurological disorder, symptom or disease is caused by intracerebral hemorrhage or a hemorrhagic stroke.

In another embodiment, the administering step is performed within 1 hour or within 2 hours before the occurrence of the neurological disorder, symptom or disease.

In another embodiment, the administering step is performed no more than or no later than 5 hours, or no more than or no later than 6 hours after the occurrence of the neurological disorder, symptom or disease.

In another embodiment, the administering step is performed within 3 hours after the occurrence of the neurological disorder, symptom or disease.

The antibody specific against the Cav-1 may be a polyclonal antibody raised against the caveolin-1. The caveolin-1 may be of human origin.

In another embodiment, the antibody specific against the Cav-1 is a polyclonal antibody raised against a peptide mapping at the N-terminus of caveolin-1 of human origin.

The antibody specific against the Cav-1 may be a monoclonal antibody. It may be a monoclonal antibody specifically raised against Cav-1 of human origin.

The administering step may be via intracerebroventricular (i.c.v.) or intravenous injection.

In one embodiment, the neurological disorder, symptom or disease is at least one selected from the group consisting of brain hemorrhage, brain injury, brain inflammation, brain edema, apoptotic neurons, hemispheric atrophy, and a motor deficit.

In another aspect, the invention relates to a method for reducing cerebral inflammation, brain tissue damage, brain neuronal death, and improving behavioral outcomes or functional recovery related to a hemorrhagic stroke in a subject in need thereof. The method comprises administering to the subject in need thereof a composition comprising:
(a) a therapeutically effective amount of an antibody specific against caveolin-1 (Cav-1) or an antigen-binding fragment thereof; and
(b) a pharmaceutically acceptable carrier,
to reduce the cerebral inflammation, brain tissue damage, brain neuronal death, and improve the behavioral outcomes or functional recovery related to the hemorrhagic stroke in the subject in need thereof.

The behavioral outcomes may be at least one selected from the group consisting of a neurological behavioral outcome and an asymmetric motor behavioral outcome.

In another embodiment, the behavioral outcomes or functional recovery is at least one selected from the group consisting of modified neurological severity score (mNSS) and elevated body swing test (EBST) ratio.

Yet in another aspect, the invention relates to a method for treating a hemorrhagic stroke in a subject in need thereof. The method comprises administering to the subject in need thereof a composition comprising:

(a) a therapeutically effective amount of an antibody specific against caveolin-1 (Cav-1) or an antigen-binding fragment thereof; and (b) a pharmaceutically acceptable carrier, to treat the hemorrhagic stroke in the subject in need thereof.

In another embodiment, the administering step is performed within 1-24 hours or within 3-24 hours window of the occurrence of the hemorrhagic stroke.

Further in another embodiment, the antibody specific against the Cav-1 is a fully human monoclonal antibody.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
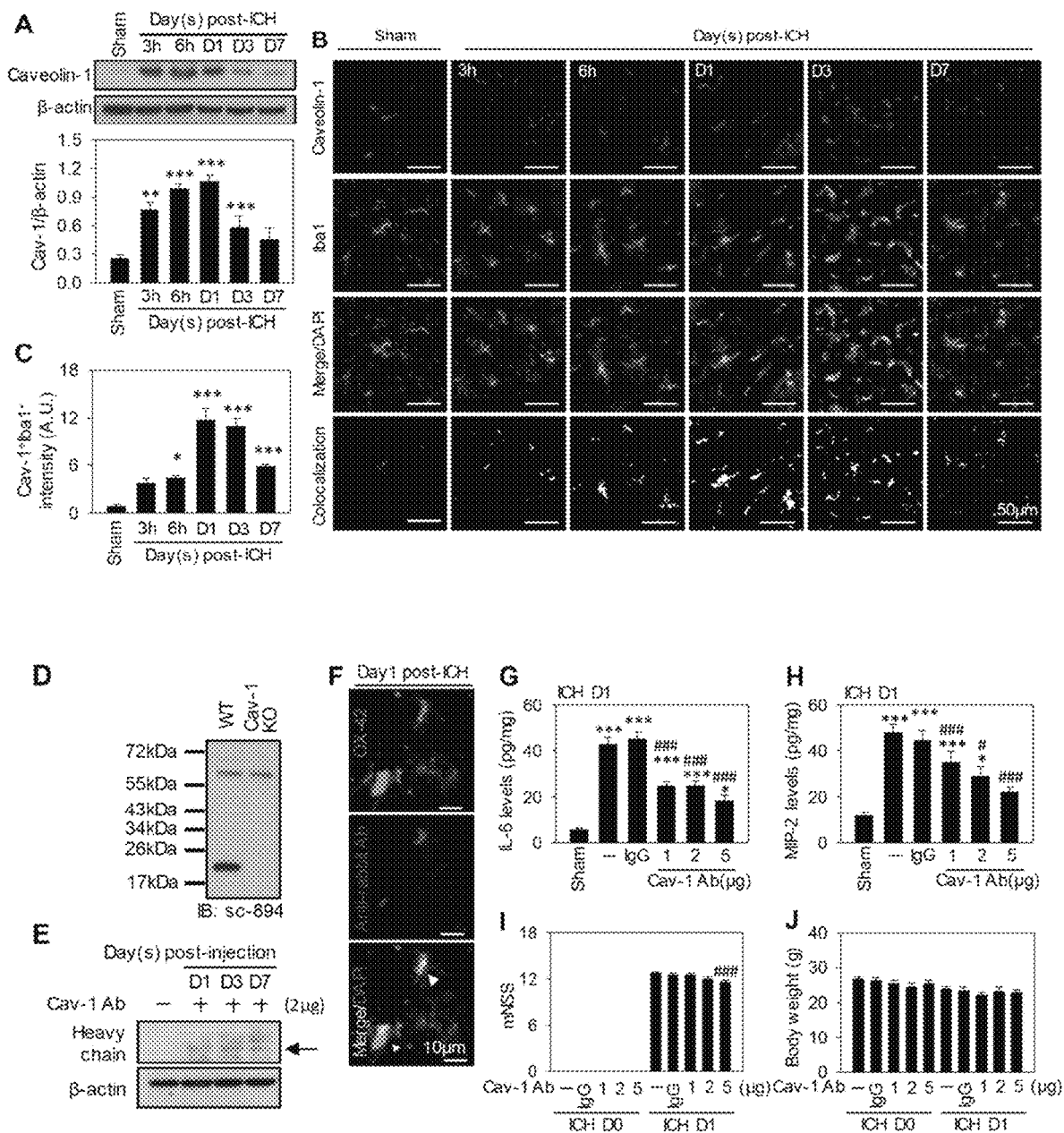
FIG. 1 shows Cav-1 induction and effect of anti-Cav-1 Ab treatment in brain tissue after ICH. (A) Expression of Cav-1 was examined by western blotting 3 hours to 7 days after ICH (n=5-6). (B, D-J) Anti-Cav-1 Ab or control IgG was icv injected 1 hour before ICH. (B) Expression of Cav-1 in microglia was detected and quantified by fluorescent colocalization of Cav-1$^+$/Iba-1$^+$ cells 3 hours to 7 days after ICH (n=5). Scale bar=50 μm. (C) Western blotting of Cav-1 in wild-type (WT) and Cav-1 knockout (KO) brain lysates. (E) Western blotting of anti-Cav-1 Ab heavy chain levels in brain lysate with anti-rabbit IgG Ab. (F) Detection of anti-Cav-1 Ab in microglia by fluorescent colocalization with anti-rabbit IgG Ab and OX-42 Ab (anti-CD11-b/c Ab). (G) IL-6 and (H) MIP-2 levels were measured by ELISA 1 day after ICH (n=6). Behavioral outcomes of (I) mNSS and (J) body weight were measured in mice injected with control IgG or 1 to 5 μg of anti-Cav-1 Ab 1 day after CH. Sections were stained with DAPI to show all nuclei. A.U., arbitrary unit; mNSS, modified neurological severity score. Values are mean±SEM. *p<0.05, *p<0.01 and **p<0.00 compared to sham group. $^\#$p<0.05, $^{\#\#}$p<0.01 and $^{\#\#\#\#}$p<0.001 compared to ICH IgG group.

The term "antibody" as used herein includes any monoclonal antibody, polyclonal antibody, multispecific antibody, or bispecific (bivalent) antibody that binds to a specific antigen.

The term "treating" or "treatment" refers to administration of an effective amount of a therapeutic agent to a subject in need thereof, who has the disease, or a symptom or predisposition toward such a disease, with the purpose of cure, alleviate, relieve, remedy, or ameliorate the disease, the symptoms of it, or the predisposition towards it. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The terms "brain injury" and "brain tissue damage" are interchangeable.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$$HED=\text{animal dose in mg/kg} \times (\text{animal weight in kg/human weight in kg})^{0.33}.$$

Caveolin-1 (N-20), referring to sc-894 antibody (SANTA CRUZ Biotech, Inc., CA, US), is an affinity purified rabbit polyclonal antibody raised against a peptide mapping at the N-terminus of caveolin-1 of human origin.

By 1-24 hours it meant that all tenth and integer unit amounts within the range are specifically disclosed as part of the invention. Thus, 1, 1.1, 1.2, 1.3, . . . 1.7, 1.8, 1.9, 2, . . . 23.8, 23.9 and 24 unit amounts are included as embodiments of this invention.

By 3-24 hours it meant that all tenth and integer unit amounts within the range are specifically disclosed as part of the invention. Thus, 3, 3.1, 3.2, 3.3, . . . 3.7, 3.8, 3.9, 4, . . . 23.8, 23.9 and 24 unit amounts are included as embodiments of this invention.

By "within 1-24 hours window of the occurrence" it meant that within 1-24 hours before or after the occurrence".

By "within 3-24 hours window of the occurrence" it meant that within 3-24 hours before or after the occurrence".

The invention relates to discovery that inhibition of Cav-1 by anti-Cav-1 antibody (Ab) treatment has a protective role in mouse ICH model. Pre- or delayed-treatment of anti-Cav-1 Ab reduces inflammation and brain damage after ICH.

EXAMPLES

Materials and Methods

Animals

Adult male C57BL/6J mice (age 8-12 weeks, weight 22-28 g) were housed in specific pathogen free environment with temperature and humidity control. All animal procedures and experimental protocols was following the Guide for the Care and Use of Laboratory Animals published by the US National Institutes of Health.

Experimental ICH Model

Briefly, mice were anesthetized with sodium pentobarbital and placed in a stereotaxic frame. After retracting the scalp, a dental drill-trephine was used to make a 1.0-mm burr hole, 0.8 mm anterior to the bregma and 2.5 mm to the right of midline. To induce ICH, bacterial collagenase (0.075 U in 0.5 μL of saline; type VII-S, SIGMA®) was injected through a 30-gauge needle on a Hamilton syringe which was implanted into the right striatum using stereotactic coordinates: +0.8 mm anterior and +2.5 mm lateral to bregma, to a depth of 2.5 mm and at a rate of 0.05 μl/min via a micro-infusion pump over 10 min. The needle was left in place for additional 20 min to prevent reflux. After needle removed, the craniotomy was sealed with dental cement and the scalp was sutured closed. Mice were maintained at 37±0.5° C. using a heated pad throughout the surgery and placed in a warm environment for recovering. Sham-operated mice received an equal volume of normal saline using the same manner.

Intracerebroventricular and Intravenous Injection

Briefly, a 30-gauge needle of a Hamilton syringe was inserted into the lateral ventricle using stereotactic coordinates: −0.5 mm anterior and +1.0 mm lateral to bregma, to a depth of 2.0 mm and Ab was infused at a rate of 0.25 L/min. Then, rabbit control IgG (5 µg/2.5 µl; sodium azide free; I5006, SIGMA-ALDRICH®) or anti-Cav1 Ab (5 µg/2.5 µl; sodium azide free; sc-894, Santa Cruz, S.C.) was infused by a micro-infusion pump for 10 min. The needle was removed 50 min after the infusion to prevent reflux, and the ICH procedure was performed 1 hour after Ab injection. For intravenous injection, 20 µg of Ab in 100 µL of saline was injected through tail vein 3 hours after ICH.

Neurological Deficit Assessment Test

Modified neurological severity score (mNSS) was applied to evaluate the functional defect by assessing motor, sensory, reflex, and balance tests (total 18 points) as described by Wu et al. (*J Neuroinflammation* 2016, 13:62) which is incorporated herein by reference. A higher score represented a more severe injury.

Body Swing Measurement Test

The elevated body swing test (EBST) for evaluating asymmetrical motor behavior was conducted with slight modifications. Mice were suspended vertically by the tail, inverted approximately 1 inch from the floor. The frequency and direction of the swing behavior was recorded for 30 s. A swing was counted when the animal moved its head>10 degrees away from the vertical axis to either side. ICH mice exhibited significantly biased swing activity toward the direction contralateral to the hemorrhagic side. The total number of swings made to the left side was divided by the total number of swings to obtain the percentages of the left bias of the swings.

Hemoglobin Measurement

The hemoglobin contents of ICH brains were quantified. Following terminal anesthesia, mice were transcardially perfused with 0.9% saline to remove intravascular blood post-ICH. After that, both ipsilateral and contralateral hemispheres of mice brain were collected and PBS buffer (300 µL) was added to each hemisphere, followed by sonication on ice for 1 min, and centrifugation at 13,000 rpm for 30 min at 4° C. Drabkin reagent (80 µL) was added to a 20-µL aliquot of supernatant and allowed to stand for 15 min at room temperature (avoid from light). Optical density was then measured at a wavelength of 540 nm to assess the concentration of cyanmethemoglobin. For standard curve, blood was collected by cardiac punctures in anesthetized control mice. Incremental volumes of this blood (0, 0.5, 1.0, 2.0, 4.0, and 8.0 µL) were then added to 300 µL of tissue lysate from a normal hemispheric sample.

Brain Water Content Measurement

Brain water content was assessed to represent brain edema. Following terminal anesthesia, mice were decapitated after ICH. The brains were immediately removed and divided into five parts, consisting of the ipsilateral and contralateral cortexes, ipsilateral and contralateral basal ganglia, and the cerebellum (which served as an internal control). Brain samples were immediately weighed to obtain the wet weight and then dried at 100° C. for 24 h to obtain the dry weight. The water content of each sample was calculated using the following formula: [(wet weight−dry weight)/wet weight]×100%

Magnetic Resonance Imaging

Magnetic resonance imaging (MRI) was performed using a 3 TMRI system (TRIO 3T MRI, Siemens MAGNETOM, Germany) as previous described. Brain edema was assessed by T2-weighted images obtained on day 1 and day 4 post-injury. The parameters for the T2-weighted imaging were as follows: repetition time/echo time=3500/75 ms, matrix=125×256, field of view=25×43 mm, and section thickness=1.0 mm. The imaging plane was located across the center of the lesion site. After normalizing image intensities between pre- and post-TBI, areas of hyperintensity represent edema regions. The regions of interest (ROI) was manually outlined by a blinded operator with the ROI tool of the MRI system software (NUMARIS/4, Version syngo MR B17, Siemens MAGNETOM). Edema volumes were assessed from T2-weighted images by summing up the edema area measured from four slices and multiplying by the slice thickness (1.0 mm).

Tissue Processing for Histology

After terminal anesthesia, mice were transcardially perfused with PBS followed by 4% paraformaldehyde. Brains were removed, post-fixed in 4% paraformaldehyde overnight, and then transferred to PBS containing 30% sucrose for cryoprotection. After that brain was coronal sectioned at 10 µm in a cryostat over the entire region of injury.

Hemorrhagic Injury and Hemispheric Enlargement Analysis

Injury volume, hemispheric atrophy, striatal atrophy, and hemispheric enlargement ratio were quantified using coronal sections spaced 200 µm apart stained with cresyl violet at 20 rostral-caudal levels. Sections were analyzed using Image J software version 1.48 (Image J, National Institutes of Health, Bethesda, Md., USA). Volume measurement was computed by a summation of the areas multiplied by the interslice distance (200 µm). Hemispheric or striatal atrophy was calculated by the following formula: [(Contralateral hemisphere or striatal volume−ipsilateral hemisphere or striatal volume)/contralateral hemisphere or striatal volume]×100%. Hemispheric enlargement was calculated by the following formula: [(ipsilateral hemisphere volume−contralateral hemisphere volume)/contralateral hemisphere volume]×100%. Analysis was performed by two experimenters who were blinded to all animal groups. Inter-rater reliability was within 10%.

Immunohistochemistry

Immunohistochemical analysis was carried out. After quenching of endogenous peroxidase activity and blocking of nonspecific binding, sections were allowed to react with the primary Abs [rabbit anti-myeloperoxidase (MPO, a neutrophil marker; Dako), rabbit anti-ionized calcium-binding adaptor molecule 1 (Iba-1, a microglia/macrophage marker; Wako)] at 4° C. overnight. Sections were then incubated with secondary anti-rabbit Ab (Santa Cruz) for 2 hours, colorimetric detection was processed according to the instructions of a Vectastain Elite ABC Kit (Vector Laboratories) with the use of diaminobenzidine as a peroxidase substrate. The specificity of the staining reaction was assessed in several control procedures, including omission of the primary Ab and substitution of the primary Ab with non-immune rabbit serum.

Double Immunofluorescence

To assess the cellular localization of Cav-1, double immunofluorescence labeling was performed by simultaneous incubation of either mouse anti-Cav-1 or rabbit anti-Cav-1 (Santa Cruz) with mouse monoclonal CD11b/c antibody (OX42, microglia/macrophage marker, GeneTex), mouse anti-neuronal nuclei antigen (NeuN, a neuronal marker; Millipore), rabbit anti-Iba-1 (Wako), rat anti-glial fibrillary acidic protein (GFAP; an astrocyte marker; Invitrogen), or CD31 (an endothelial cell marker, BD Biosciences Pharmigen) overnight at 4° C. To assess different types of microglia activation, immunostaining was performed by incubation of rabbit anti-ba-1 with rat anti-CD16/32 (BD biosciences), mouse anti-CD206 (Bio Rad), mouse anti-arginase 1 (ARG1, BD sciences), or CCR2 (macrophage marker, Novus) overnight at 4° C. Sections were then washed, incubated with Alexa Fluor 488- or Alexa Fluor 594-conjugated secondary Abs (Molecular Probes) for 2 h and observed under a fluorescence microscope.

Fluoro-Jade B Staining

Fluoro-Jade B (FJB), a polyanionic fluorescein derivative that binds with high sensitivity and specificity to degenerating neurons, staining was performed. Briefly, sections were rehydrated in graded ethanol solutions (100% and 70%) and distilled water for 5 minutes each, incubated in 0.006% $KMnO_4$ for 30 min, rinsed in distilled water for 2 min, incubated in a 0.001% solution of FJB (Chemicon) for 30 min, and observed under a fluorescence microscope at 450-490 nm.

TUNEL Assay

Terminal deoxynucleotidyl transferase dUTP nick end labeling (TUNEL) staining was used to label apoptotic cells with fluorescein isothiocyanate (In situ Cell Death Detection Kit; Roche Molecular Biochemicals). Sections were stained with TUNEL reaction mixture containing terminal deoxynucleotidyl transferase for 60 min at 37° C., then incubated with mouse anti-NeuN overnight at 4° C. and Alexa Fluor 594-conjugated secondary Ab (Molecular Probes) for 2 h. Images were detected under a fluorescence microscope at an excitation light.

Quantification of FJB, NeuN, Iba-1 and MPO Staining

FJB, NeuN, Iba-1, and MPO staining was quantified on three consecutive sections from the hemorrhagic core at the level of 0.24 mm from the bregma. The number of positive cells were counted in an area of 920×860 $\mu m^2$ in 10-12 non-overlapping fields immediately adjacent to the hematoma using a magnification of ×200. Iba-1-positive resting microglia/macrophages was defined as resting if they contained relatively small cell bodies (<7.5 μm in diameter) with long slender processes. Microglia/macrophages were defined as activated when a cell body increased in size compared to resting microglia with short, thick processes and intense immunointensity. Activated microglia/macrophages were defined based on a combination of morphological criteria and a cell body diameter cutoff of 7.5 μm. The total number of NeuN-, FJB-, Iba-1-, and MPO-positive cells were expressed as the mean number per field of view. Analysis was performed by two experimenters who were blinded to all animal groups. Inter-rater reliability was within 10%.

Quantitative Immunocolocalization Analysis

Colocalization of Cav-1 with Iba-1 or Iba-1 with CD16/32, CD206 or ARG1 was analyzed. Briefly, colocalized signal in merged images was turned into the gray pixel map and calculated by ImageJ software. The degree of colocalization was expressed in arbitrary units.

Western Blots

A 2-mm-thick coronal section from the ipsilateral hemisphere was collected following ICH or sham surgery. Equal amounts of protein (35 to 50 μg protein in 20 μL for tissue samples and 20 μg protein in 20 μL for cell lysates) was separated by sodium dodecyl sulfate-polyacrylamide gels, transferred to Immobilon-P membranes, blocked using 5% milk in PBS containing 0.1% TWEEN®-20, and probed overnight at 4° C. with primary Abs. Rabbit anti-iNOS and rabbit anti-COX-2 were from Cayman Chemical. Rabbit anti-cleaved caspase-3, rabbit anti-phospho-p38, rabbit anti-total p38), rabbit anti-phospho-extracellular signal-regulated kinases p44/42, rabbit anti-total Erk, rabbit anti-phospho-Jun amino-terminal kinases (JNK, Thr183/Tyr185), rabbit anti-total JNK, rabbit anti-phospho-P65, rabbit anti-phospho-c-Jun and rabbit anti-c-Jun were from cell signaling. Mouse anti-β-actin was from SIGMA-ALDRICH®. The membrane was then incubated with horseradish peroxidase-linked anti-rabbit or anti-mouse secondary Ab for 1 h at 4° C. Protein band intensities were quantified using Image J software, and the relative intensity of protein signals were normalized to the corresponding f-actin intensity.

Enzyme-Linked Immunosorbent Assay and Nitrite Assay (ELISA)

Brain samples were collected as in western blotting after surgery. Macrophage inflammatory protein-2 (MIP-2), interleukin (IL)-6, IL-1β, IL-4 and IL-10 were measured in brain homogenates or cell lysates using a commercially available ELISA kit (R&D Systems). All samples and standards were assayed in duplicate according to the manufacturer's instructions. Nitric oxide (NO) production was assessed by measuring the nitrite levels of the culture supernatants with Griess reagent (SIGMA®).

Microglial Cell Line Culture

The BV2 mouse microglia cells were cultured in Dulbecco's modified Eagle's media (DMEM; Gibco/BRL) supplemented with 10% heat-inactivated fetal bovine serum (FBS; Gibco/BRL), 100 U/mL penicillin and 100 μg/mL streptomycin in a humidified atmosphere of 5% $CO_2$ at 37° C. BV2 microglia were stimulated with either 0.1 μg/mL LPS, or 10 U/mL thrombin in the absence or presence of varying concentrations of anti-Cav-1 Ab (sc-594, Santa Cruz) for 24 h. The experiments were repeated four times with different batches of cultures.

Mouse Primary Microglial Culture

The mouse primary microglial cells were obtained from P7 post-natal mice brain striatum and cultured in Roswell Park Memorial Institute's media (RPMI; Gibco/BRL, Bethesda, Md., USA) supplemented with 10% heat-inactivated fetal bovine serum (FBS; Gibco/BRL), 100 U/mL penicillin and 100 μg/mL streptomycin in a humidified atmosphere of 5% $CO_2$ at 37° C. Microglial cells were ready for use after 14 days culture and stimulated with 10 U/mL thrombin+100 ng/mL IFN-γ in the absence or presence of anti-Cav-1 Ab for 24 h. The experiments were repeated four to five times with independent cultures.

Statistical Analyses

All data are presented as the mean k standard error of the mean (SEM). One-way or two-way analysis of variance (ANOVA) followed by post-hoc Bonferroni test evaluation was used for multiple groups to determine significant differences. Student's 1-test was used to test the differences between two groups. Statistical significance was set at $P<0.05$.

Results

Increased Cav-1 Protein Expression in Microglia/Macrophages after ICH

Figure 8:
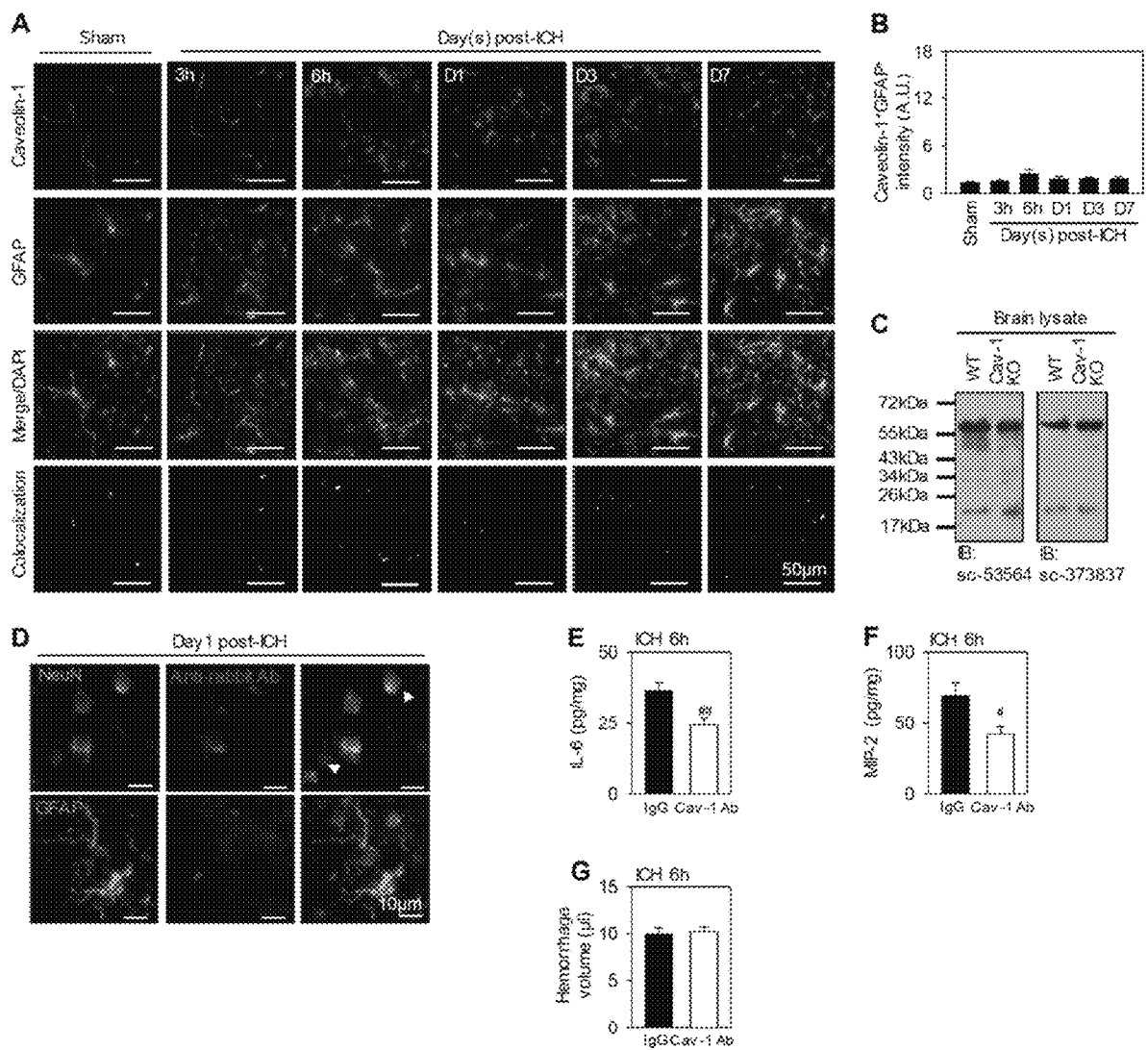
FIG. 8 shows expression of Cav-1 and effect of anti-Cav-1 Ab treatment after ICH. (A, B) Expression of Cav-1 in astrocytes was detected and quantified by fluorescent colocalization of $Cav-1^+/GFAP^+$ cells 3 hours to 7 days after ICH (n=5). Scale bar=50 μm. (C) Western blotting of Cav-1 in wild-type (WT) and Cav-1 knockout (KO) brain lysates with different anti-Cav-1 Abs. Scale bar=50 μm. (D) Detection of anti-Cav-1 Ab in neurons and astrocytes by fluorescent colocalization of anti-rabbit IgG Ab and NeuN or GFAP. Scale bar=10 μm. (E) IL-6 and MIP-2 levels were measured by ELISA 6 hours after ICH (n=6). (F) Hemorrhage volume was evaluated by hemoglobin assay 6 hours after ICH (n=6).

The induction of Cav-1 at 3 hours to 7 days after ICH by western blot analysis was examined. ICH induced an increase in Cav-1 protein level in the hemorrhagic hemisphere at 3 hours, 6 hours, 1 day and 3 days (303%, 392%, 423% and 231% of the sham level, respectively; FIG. 1A). The level was peaking at 1 day and then decreased at 3 days. At 7 days after ICH, the Cav-1 protein level was slightly increased but was not significantly different from the sham control level (178% of the sham level; P=0.079). Double-immunofluorescent staining was used to examine Cav-1 expression in microglia/macrophages in the brain after ICH. Cav-1 was significantly induced in microglia/macrophages at 6 hours, 1 day, 3 days and 7 days after ICH (526%, 1425%, 1327% and 699% of the sham level), with a peak at 1 and 3 days (FIGS. 1B-C). We examined colocalization levels of Cav-1 with GFAP+ cells, and the results showed that Cav-1 protein was rarely expressed in astrocytes in the sham control brain or after ICH (FIGS. 8A-B). The data suggest that Cav-1 may be involved in ICH-induced microglial/macrophage activation, and this effect can be as early at 6 hours post-CH.

Anti-Cav-1 Antibody Treatment Reduces Cerebral Inflammation and Brain Tissue Damage and Improves Long-Term Behavioral Outcomes after ICH We verified the specificity of three commercial anti-Cav-1 antibodies by immunoblotting on brain samples from Cav-1 knockout mice. Of the three tested antibodies, only the sc-894 antibody did not detect the Cav-1 protein in Cav-1 knockout brain lysates (FIG. 1D), and the other two candidate antibodies still detected a Cav-1-immunoreactive band at ~22 kDa in Cav-1 knockout brain lysates (FIG. 8C). Thus, we chose the sc-894 antibody (anti-Cav-1 antibody) for the following experiments. The anti-Cav-1 antibody was delivered by intracerebroventricular (i.c.v) injection 1 hour before ICH. Western blotting of anti-Cav-1 Ab with anti-rabbit IgG Ab showed an immunoreactive band at ~55 kDa corresponding to the heavy chain in brain lysates up to 7 days following icv injection (FIG. 1E), suggesting that the anti-Cav-1 antibody can be maintained for the brain for over 7 days. The rabbit IgG staining was observed in microglia/macrophage (FIG. 1F) and neurons but not in astrocytes (FIG. 8D) at 1 day after icv injection. We then investigated the anti-inflammatory effects of anti-Cav-1 antibody. Treatment with 1, 2, and 5 µg/2.5 µL Cav1-antibody were all able to reduce cytokine expression of IL-6 (FIG. 1G) and MIP-2 (FIG. 1H) at 1 day post-ICH and the dose of 5 µg/2.5 µL had the best effect. Only the dose of 5 µg/2.5 µL decreased mNSS scores at 1 day after ICH (FIG. 1I) and there were no body weight changes following different doses of anti-Cav-1 antibody injection (FIG. 1J). Therefore, we used the dose of 5 µg/2.5 µL for subsequent experiments. At 6 hours after ICH, treatment with 5 µg/2.5 µL anti-Cav-1 antibody reduced expression of IL-6 (FIG. 8E) and MIP-2 (FIG. 8F) as well.

Figure 2:
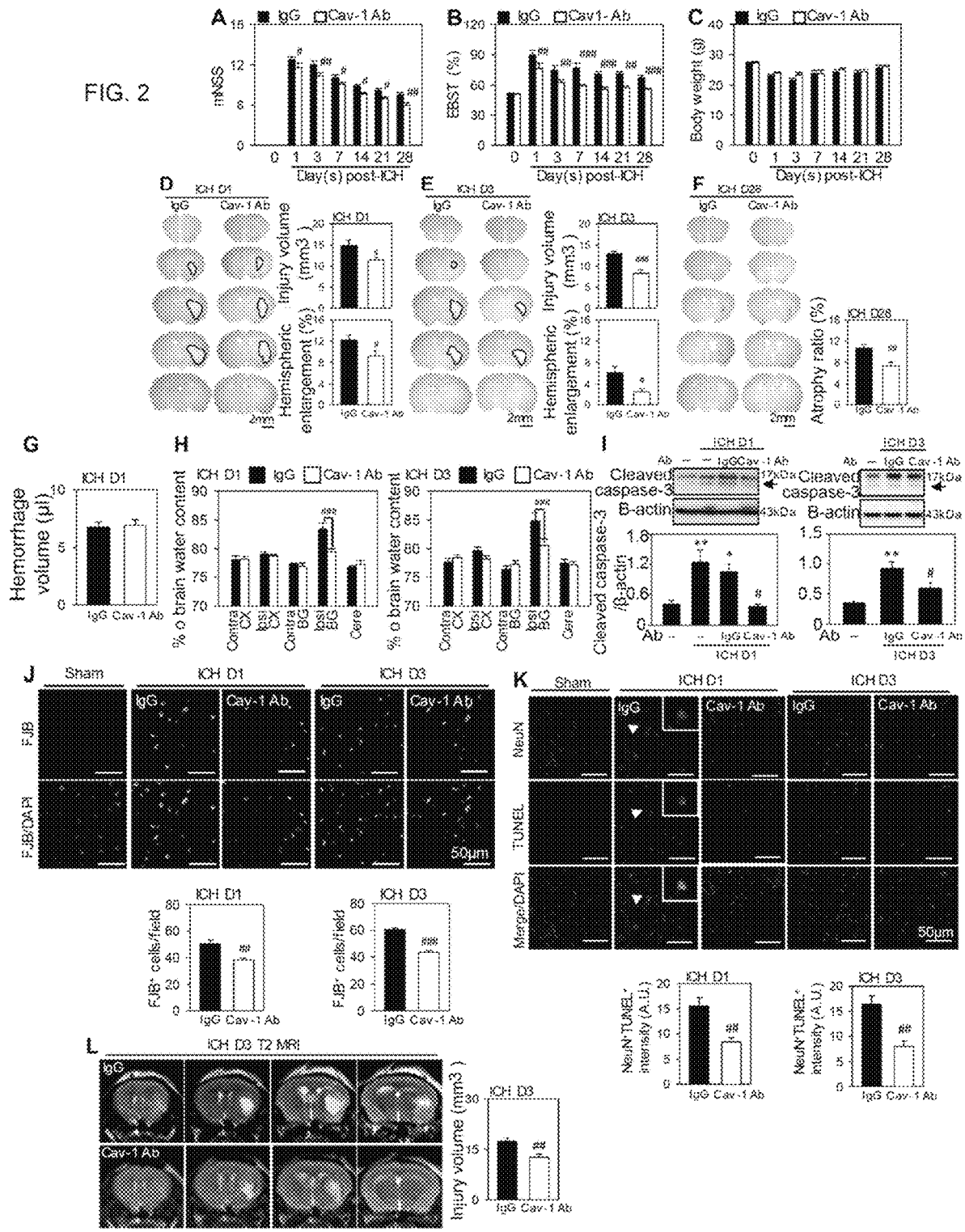
FIG. 2 shows anti-Cav-1 Ab treatment improves behavioral outcome and reduces brain edema and neuron death after ICH. Anti-Cav-1 Ab or control IgG was icv injected 1 hour before ICH. Behavioral outcomes of (A) mNSS and (B) EBST and (C) body weight were measured 1 to 28 days after ICH (n=8). (D, E) Injury volume and hemispheric enlargement ratio were examined by cresyl violet staining 1 and 3 days after ICH (n=8). (F) Atrophy ratio was analyzed by cresyl violet staining 28 days after ICH (n=8). Scale bar=2 mm. (G) Hemorrhage volume was evaluated by hemoglobin assay 1 day after ICH (n=6). (H) Brain edema level was quantified by brain water content, 1 and 3 days after ICH (n=8). (1) Cleaved caspase-3 was detected by western blotting 1 and 3 days after ICH (n=5-6). (J) Degenerated neuron was examined by FJB staining 1 and 3 days after ICH (n=8). Scale bar=100 m. (K) Apoptotic neurons were detected and quantified by fluorescent colocalization of TUNEL$^+$/NeuN+ cells 1 and 3 days after ICH (n=6). (L) Injury volume was detected by MRI, 3 days after ICH (n=6). Sections were stained with DAPI to show all nuclei. Contra, contralateral side; Ipsi, ipsilateral side; CX, cortex; BG, basal ganglia; Cere, cerebellum. Values are mean±SEM. *p<0.05, *p<0.01 and *p<0.001 compared to sham or control group. $^\#$p<0.05, $^{\#\#}$p<0.01 and $^{\#\#\#\#}$p<0.001 compared to ICH IgG group.

As most patients with ICH are left with motor disability, we evaluated the long-term functional outcomes. Mice treated with anti-Cav-1 antibody showed better mNSS and ratio of EBST than the control group up from 1 day to 28 days post-ICH (FIGS. 2A-B), whereas, both mouse groups had similar body weight changes (FIG. 2C). To determine whether the observed changes in functional recovery were reflected in a reduction of brain tissue damage and neuronal death, histological outcomes were evaluated. Cresyl violet staining showed that anti-Cav-1 antibody treatment significantly reduced hemorrhagic injury volumes by 22% and 34% compared with the vehicle group at 1 day and 3 days, respectively (FIGS. 2D-E). Hemispheric enlargement, an indicator of brain edema, was also significantly smaller in anti-Cav-1 antibody-treated mice than in vehicle-treated mice at both 1 day ($9.21\pm0.99\%$ versus $12.22\pm0.93\%$; FIG. 2D) and 3 days ($2.53\pm0.57\%$ versus $6.12\pm1.12\%$; FIG. 2E). We further evaluated whether anti-Cav-1 antibody treatment attenuated brain tissue damage during the chronic stage of ICH. Consistent with the protective effect at the acute stage, anti-Cav-1 antibody treatment significantly reduced the ratio of hemispheric atrophy at 28 days ($7.34\pm0.71\%$ versus $10.71\pm0.70\%$; FIG. 2F). However, the anti-Cav-1 antibody did not affect hematoma size at either 6 hour (FIG. 8G) or 1 day (FIG. 2G), a major prognostic indicator in clinical ICH, indicating that the protective effects of Cav-1 inhibition is independent of clot formation.

Anti-Cav-1 Antibody Treatment Reduces Brain Edema and Neuron Death after ICH

Figure 9:
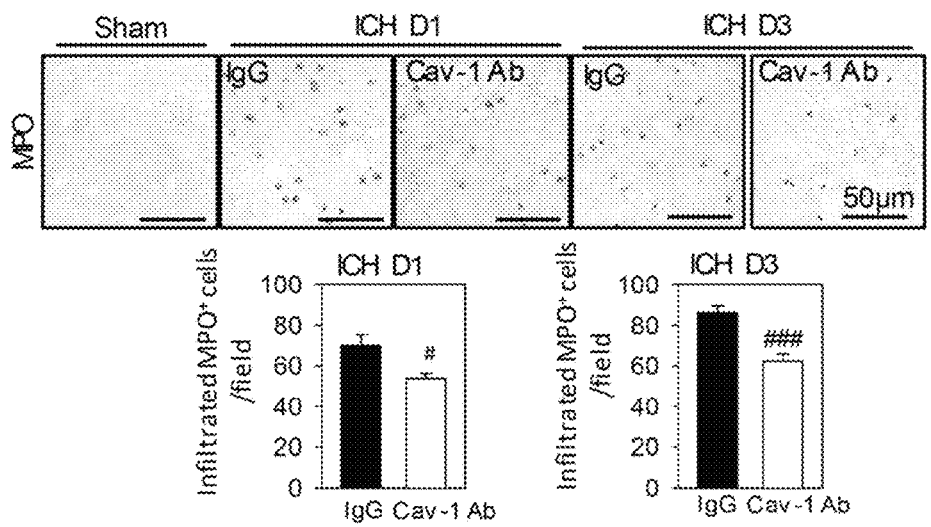
FIG. 9 shows anti-Cav-1 Ab treatment reduces neutrophil infiltration after ICH. Neutrophil infiltration was detected by MPO staining 1 day and 3 days after ICH.

Brain water content was significantly decreased in the ipsilateral basal ganglion in the anti-Cav-1 antibody group compared with the IgG group at both 1 day ($79.47\pm0.52\%$ versus $83.43\pm1.05\%$) and 3 days ($80.56\pm1.17\%$ versus $84.84\pm1.32\%$) post-ICH (FIG. 2H). Neutrophil infiltration, a major consequence of blood-brain-barrier breakdown and brain edema, was also reduced following administration of anti-Cav-1 antibody compared with IgG administration at both 1 day ($53.80\pm2.57$ versus $69.76\pm5.50$ cells/field) and 3 days ($62.27\pm3.57$ versus $86.21\pm3.18$ cells/field) (FIG. 9).

The level of cleaved caspase-3, a final effector of apoptotic death, was significantly decreased following anti-Cav-1 antibody treatment at both 1 day (46% of the IgG-level) and 3 days (51% of the IgG-level) (FIG. 2I). Anti-Cav-1 antibody treatment significantly attenuated the number of degenerative neurons (FJB+ cells; $38.25\pm1.44$ versus $50.30\pm2.94$ cells/field for 1 day and $43.43\pm1.24$ versus $60.44\pm1.33$ cells/field for 3 days; FIG. 2J) and the signal of apoptotic neurons (TUNEL+/NeuN+ cells) around the hematoma when compared to IgG administration at both 1 day and 3 days (FIG. 2K). MRI was applied to assess the degree of brain damage on live animals and showed that the lesion volume was significantly decreased in the anti-Cav-1 antibody-treated group compared with the IgG control ($12.63\pm0.96$ versus $17.40\pm0.95$ mm$^3$) at 3 days post-ICH (FIG. 2L).

Figure 3:
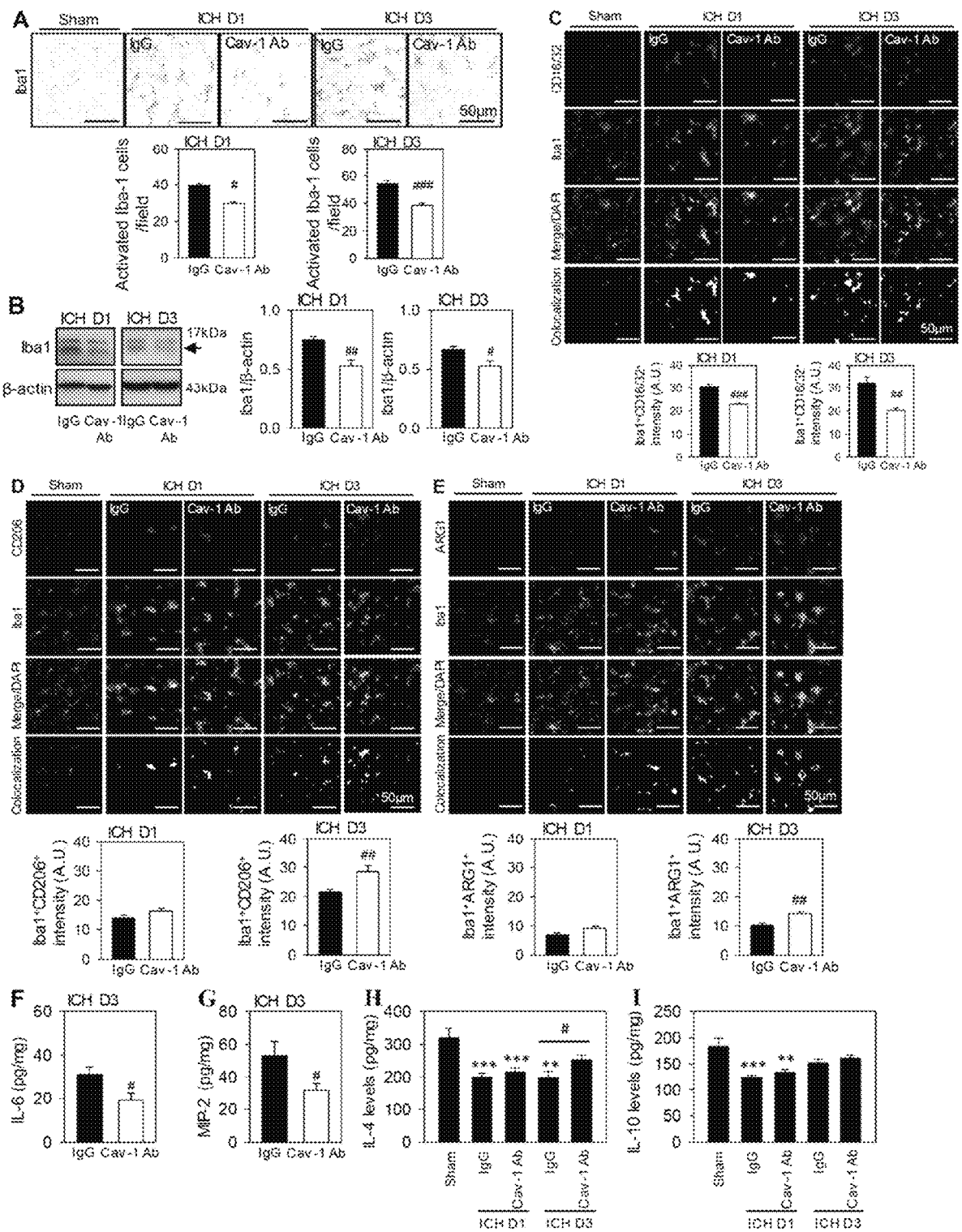
FIG. 3 shows anti-Cav-1 Ab reduced microglia activation and modulates microglia polarization from M1 to M2 phenotype after ICH. Anti-Cav-1 Ab or control IgG was icv injected 1 hour before ICH. Microglial activation was quantified by immunostaining (A) and western blotting (B) of Iba-1 expression 1 day and 3 days after ICH (n=8). (C) Classical-activated (M1-like) microglia were detected and quantified by fluorescent colocalization of CD16/32$^+$/Iba-1$^+$ cells 1 day and 3 days after ICH (n=6). (D, E) Alternative-activated (M2-like) microglia were detected by fluorescent colocalization of (D) CD206$^+$/Iba-1$^+$ and (E) ARG1$^+$/Iba-1$^+$ cells 1 and 3 days after ICH (n=6). Scale bar=50 μm. (F-I) IL-6, MIP-2, IL-4 and IL-10 levels were examined by ELISA 3 days after ICH (n=7-8). Sections were stained with DA PI to show all nuclei. ARG1, arginase1. Values are mean±SEM. p<0.01 and *p<0.001 compared to sham group. $^\#$p<0.05, $^{\#\#}$p<0.01 and $^{\#\#\#\#}$p<0.001 compared to ICH IgG group.

Anti-Cav-1 Antibody Treatment Reduces Proinflammatory M1 Microglial/Macrophage Activation and Heightens Anti-Inflammatory M2 Microglia/Macrophage Response after ICH Activated microglia/macrophages (cell body enlarged Iba-1$^4$ cells) were observed around hematoma at both 1 and 3 days, and the number of activated microglia/macrophages was significantly reduced in anti-Cav-1 antibody-treated mice compared with the IgG control at 1 day ($29.63\pm0.89$ versus $39.64\pm0.90$ cells/field) and 3 days ($38.56\pm1.70$ versus $54.16\pm2.56$ cells/field) (FIG. 3A). Protein expression of Iba-1 was also decreased following anti-Cav-1 antibody treatment (FIG. 3B). By immunofluorescent staining microglia phenotypes were determined with the markers of classically activated M1 microglia/macrophage (CD16/32) or alternatively activated M2 microglia/macrophage (CD206, ARG1). While no CD16/32+/Iba-1+, CD206+/Iba-1+ or ARG1+/Iba-1+ cells were observed in sham-operated brains, ICH induced an increase of CD16/32+/Iba-1+, CD206+/Iba-1+ and ARG1+/Iba-1+ cells in the perihematomal area at both 1 and 3 days (FIGS. 3C-E). The CD16/32+/Iba-1+ signal in the perihematomal area was significantly decreased at both 1 day and 3 days, and the CD206+/Iba-1+ and ARG1+/Iba-1+ signals were both increased in anti-Cav-1 antibody treated mice at 3 days post-ICH (FIGS. 3C-E). In accordance with declined M1 polarization elevating M2 phenotype after anti-Cav-1 antibody treatment, treatment with anti-Cav-1 antibody reduced the expression of proinflammatory cytokines, IL-6 and MIP-2 (FIGS. 3F-G), and increased the expression of anti-inflammatory cytokines, IL-4 and IL-10, at 3 days post-ICH (FIGS. 3H-I). These results indicated that inhibition of Cav-1 reduced ICH-induced microglial/macrophage activation and modulating microglia/macrophage polarization from proinflammatory to anti-inflammatory state.

Figure 4:
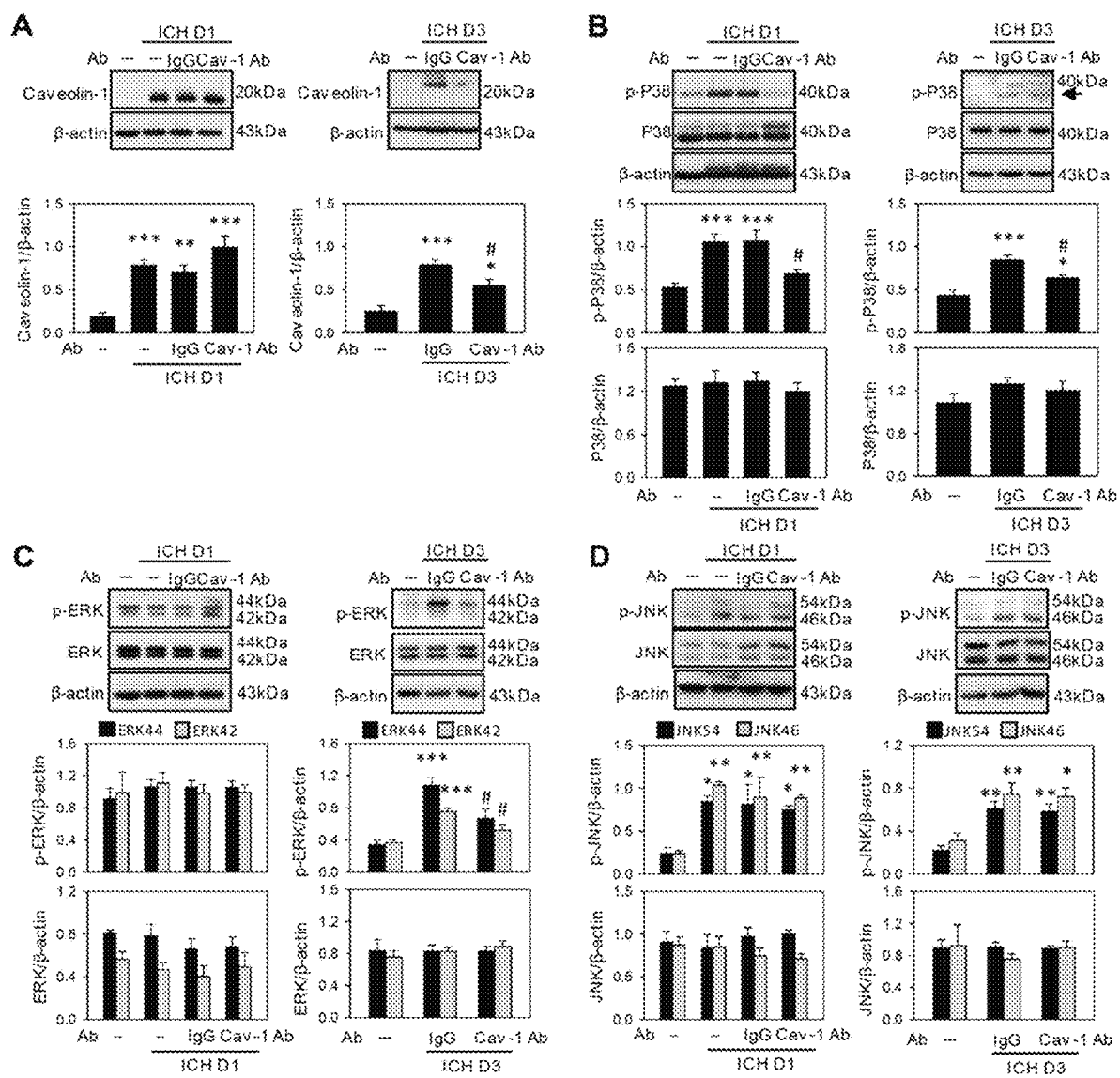
FIG. 4 shows anti-Cav-1 Ab treatment inhibits Cav-1 expression and suppressed P38 and ERK signaling following ICH. Anti-Cav-1 Ab or control IgG was icv injected 1 hour before ICH. (A) Cav-1, (B) P38 phosphorylation, (C) ERK phosphorylation, and (D) JNK phosphorylation levels were examined and quantified by western blotting 1 day and 3 days after ICH. Values are mean±SEM. (n=5-6). *p<0.05, p<0.01 and *p<0.001 compared to sham or control group. $^\#$p<0.05 compared to ICH IgG group.

Anti-Cav-1 Antibody Treatment Reduces Cav-1 Induction and Activation of MAPK Signaling after ICH ICH induced an increase in Cav-1 protein expression and phosphorylation of P38 and JNK at both 1 day and 3 days (FIGS. 4A-B and 4D). The increased ERK phosphorylation was delayed to 3 days post-ICH (FIG. 4C). Anti-Cav-1 antibody treatment suppressed Cav-1 induction at 3 days, but not at 1 day after ICH (FIG. 4A). Anti-Cav-1 antibody treatment reduced the phosphorylation of P38 at 1 day and 3 days, and ERK at 3 days, but not JNK, after ICH (FIGS. 4B-D). These data indicate that the protective mechanisms of anti-Cav-1 antibody treatment against ICH may be related to inhibition of P38 and ERK activation.

Anti-Cav-1 Antibody Treatment Reduces Thrombin-Induced Inflammatory Response in Microglial Culture Via P38 MAPK Signaling Pathway.

Figure 5:
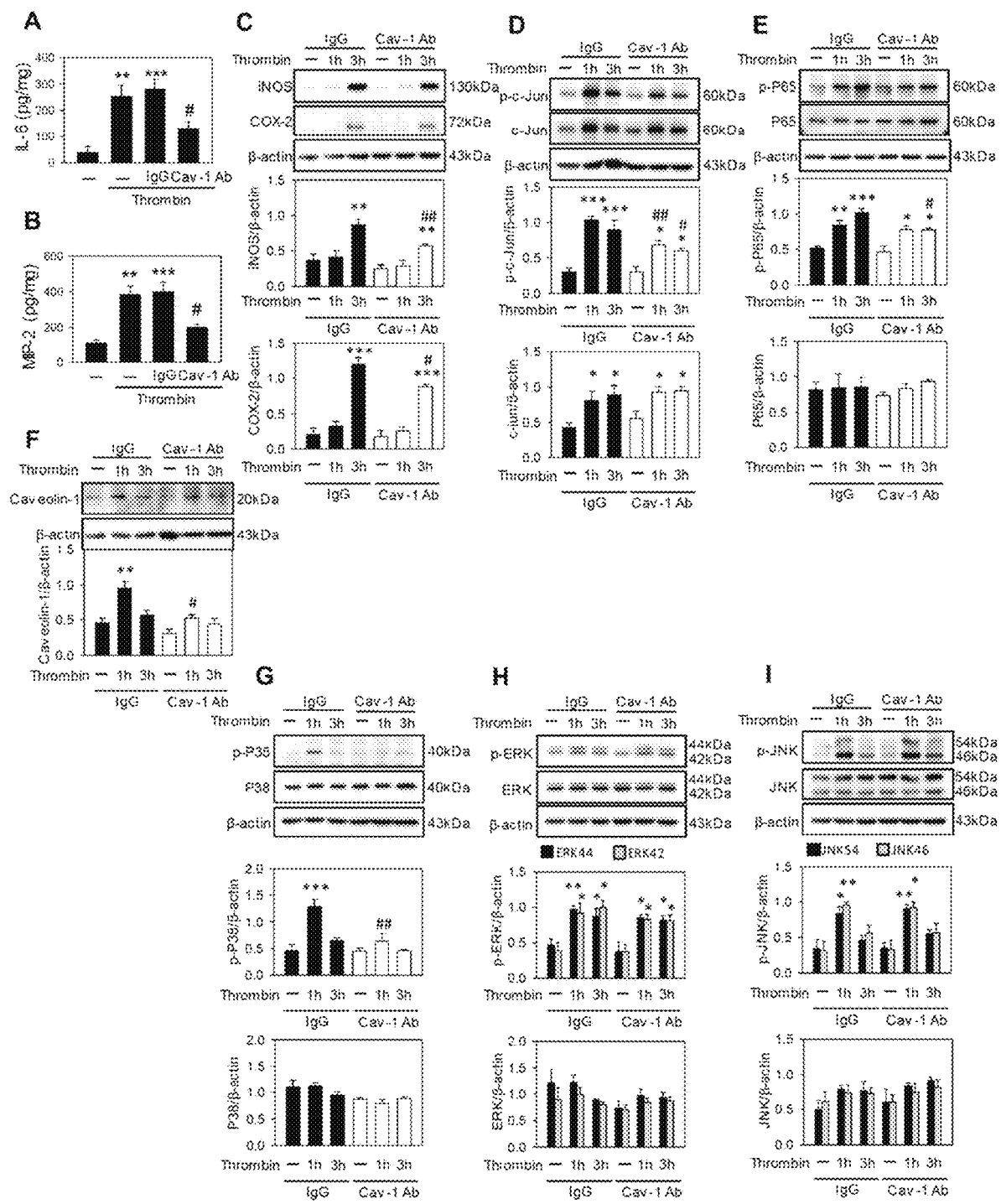
FIG. 5 shows anti-Cav-1 Ab treatment attenuates thrombin-induced inflammatory response in primary microglial culture via P38 signaling pathway. Primary microglia were treated with thrombin plus 1 μg/ml of anti-Cav-1 Ab or control IgG for 24 hours (A, B) or for 1 to 3 hours (C-1). (A, B) Thrombin-induced IL-6 and MIP-2 expression were determined by ELSA. (C-1) Thrombin-induced microglial activation were assessed by western blotting of (C) iNOS and COX-2 expression (n=3-4), (D) c-Jun phosphorylation, (E) P65 phosphorylation, (F) Cav-1 expression, (G) P38 phosphorylation, (H) ERK phosphorylation and (1) JNJ phosphorylation. Values are mean±SEM. *p<0.05, p<0.01 and *p<0.001 compared to control group. $^\#$p<0.05 and $^{\#\#\#}$p<0.001 compared to thrombin IgG group.
Figure 10:
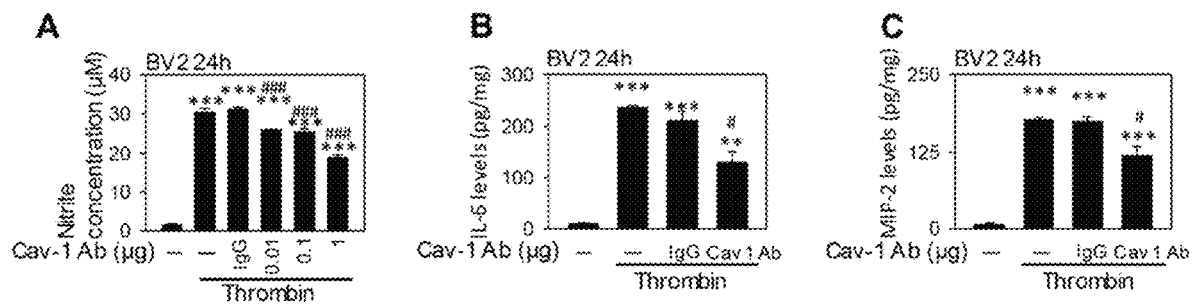
FIG. 10 shows anti-Cav-1 Ab treatment reduces thrombin-induced nitrite, IL-6 and MIP-2 production. BV2 cells were treated with thrombin plus 0.1 to 1 μg/ml of anti-Cav-1 Ab or control IgG for 24 hours. (A) Dose-dependent effect of anti-Cav-1 Ab treatment in nitrite production (n=6). (B, C) Thrombin-induced IL-6 and MIP-2 expression were determined by ELSA (n=6).

We determined the effect of Cav-1 inhibition on microglia directly using BV2 microglia cell line and primary mouse microglial culture. Thrombin, a serine protease released at high levels during coagulation in ICH, was used to activate microglia. The results showed that treatment with 10 U/mL thrombin for 24 hours induced a significant increase in nitrite production on BV2 microglia cells. Co-treatment of anti-Cav-1 antibody at doses of 0.01, 0.1, and 1 μg/mL for 24 hours significantly reduced nitrite production, and 1 μg/mL anti-Cav-1 antibody provided the highest degree of anti-inflammatory protection (FIG. 10A). Therefore, a dosage of 1 μg/mL was employed for subsequent studies. Similarly, levels of proinflammatory cytokines IL-6 and MIP-2 were reduced in the condition medium of BV2 cells following 1 μg/mL anti-Cav-1 antibody administration (FIGS. 10B-C). Similar to the effects on BV2 cells, anti-Cav-1 antibody treatment reduced levels of cytokines IL-6 and MIP-2 in the culture medium of primary mouse microglia at 24 hours after stimulation (FIGS. 5A-B). Protein expression of iNOS and COX-2, two proinflammatory enzymes, were significantly attenuated following anti-Cav-1 antibody treatment in thrombin-stimulated primary microglia at 3 hours after thrombin exposure (FIG. 5C). AP (activator protein)-1 and NF-κB are two transcription factors that induce the expression of many genes involved in cerebral inflammation and are downstream effectors of MAPK signaling. Both total c-Jun, a key member of the AP-1 family, and p-c-Jun levels increased following thrombin stimulation (FIG. 5D). However, thrombin stimulation increased only p-P65, an indicator of NF-κB activation, but did not affect total P65 level at both 1 hour and 3 hours after exposure (FIG. 5E). Treatment with anti-Cav-1 antibody significantly reduced thrombin-induced phosphorylation of P65 and c-Jun at both 1 hour and 3 hours after stimulation (FIGS. 5D-E). Anti-Cav-1 antibody directly reduced Cav-1 protein expression and P38 phosphorylation (FIGS. 5F-G) at 1 hour after thrombin stimulation. There was no difference in the phosphorylation of ERK and JNK between IgG-treated and anti-Cav-1 antibody-treated groups at either 1 hour or 3 hour after thrombin stimulation (FIGS. 5H-I). The results suggest that anti-Cav-1 antibody may inhibit proinflammatory microglial activation through suppressing P38-MAPK signaling pathway.

Figure 6:
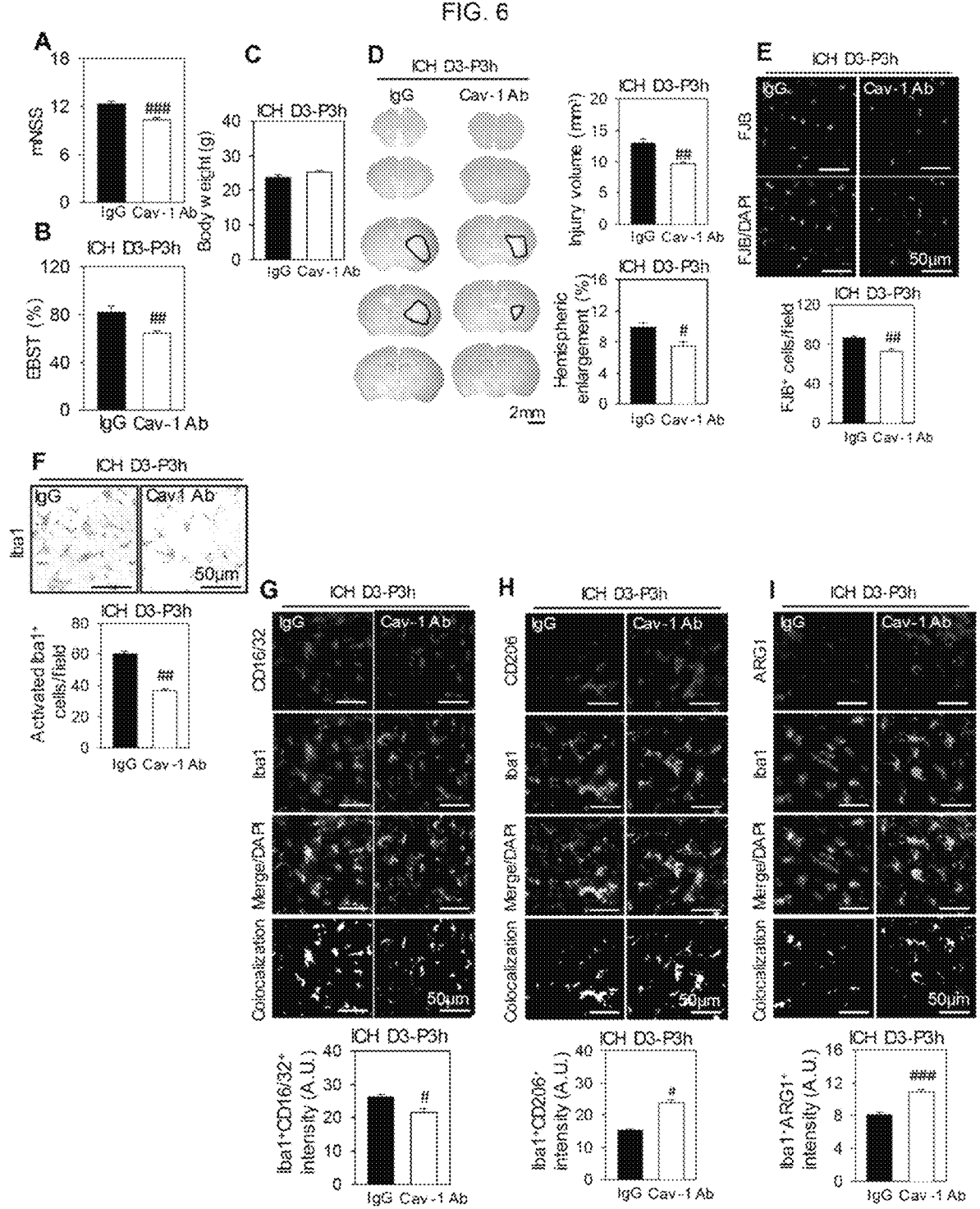
FIG. 6 shows delayed treatment with anti-Cav-1 Ab reduces brain damage and neuronal death and modulates microglia polarization from M1 to M2 phenotype after ICH. Anti-Cav-1 Ab (20 μg in 100 μl of saline) was intravenous injected through tail vein 3 hours after ICH. Behavioral outcomes of (A) mNSS and (B) EBST and (C) body weight were assessed at 1 and 3 days after ICH (n=9). (D) Injury volume and hemispheric enlargement ratio were evaluated by cresyl violet staining 3 days after ICH (n=5-6). Scale bar=2 mm. (E) Neuron degeneration, evaluated by FJB staining, and (F) microglial activation, evaluated by Iba-1 immunostaining, were assessed 3 days after ICH. (G) Classical-activated (M1-like) microglia were detected by fluorescent colocalization of CD16/32$^+$/Iba-1$^+$ cells 3 days after ICH (n=5-6). (H, I) Alternative-activated (M2-like) microglia were determined by fluorescent colocalization of (H) CD206$^+$/Iba-1$^+$ and (I) ARG1$^+$/Iba-1$^+$ cells 1 and 3 days after ICH (n=6). Scale bar=50 μm. Sections were stained with DAPI to show all nuclei. Values are mean±SEM. $^\#$p<0.05, $^{\#\#}$p<0.01 and $^{\#\#\#\#}$p<0.001 compared to ICH IgG group.
Figure 11:
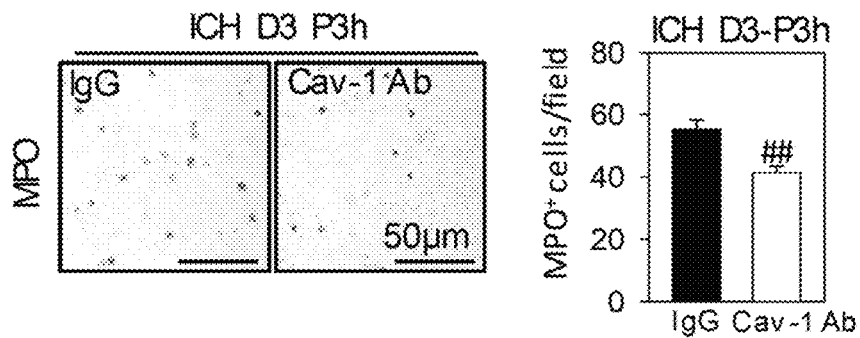
FIG. 11 shows delayed anti-Cav-1 Ab treatment reduces neutrophil infiltration after ICH. Neutrophil infiltration was detected by MPO staining 3 days after ICH.

Delayed Intravenous Anti-Cav-1 Antibody Treatment Reduces Brain Damage and Neuronal Death, and Modulates M1/M2 Polarization of Microglia/Macrophages Anti-Cav-1 antibody treatment was delayed by 3 hour after ICH onset through the intravenous route. Anti-Cav-1 antibody treatment initiated at 3 h post-ICH still significantly reduced global neurological deficits assessed by mNSS and motor asymmetry evaluated by the elevated body swing test at 3 days (FIGS. 6A-B). There was no significant difference in body weight changes between IgG-treated and anti-Cav-1 antibody-treated groups during the 3-day observation period (FIG. 6C). Delayed anti-Cav-1 antibody treatment also reduced injury volume and hemispheric enlargement, an indicator of brain edema (FIG. 6D), and attenuated the number of FJB-positive neurons (FIG. 6E) and neutrophil infiltration (FIG. 11) around the perihematoma area at 3 days post-ICH. Delayed treatment of anti-Cav-1 antibody reduced microglial/macrophage activation and CD16/32$^+$/Iba-1$^+$ signal, and increased CD206$^+$/Iba-1$^+$ and ARG1$^+$/Iba-1$^+$ signals in the perihematomal area at 3 days (FIGS. 6F-I). The data indicate that delayed inhibition of Cav-1 still exerts neuroprotective effects, and the effect may be mediated by modulating M/M2 polarization of microglia/macrophages.

Delayed Intravenous Anti-Cav-1 Antibody Treatment Modulates M/M2 Polarization of Infiltrated Macrophages To investigate whether intravenous administration of anti-Cav-1 antibody reduced infiltration of peripherally-derived macrophages, we used CCR2 staining to label macrophages. Cav-1 protein was expressed on CCR2$^+$ cells at Day 3 post-ICH (FIG. 7A). Delayed treatment of anti-Cav-1 antibody via peripheral administration reduced the number of CCR2$^+$ cells (55.15±2.13 versus 47.84±0.59 cells/field) (FIG. 7B), also reduced CD16/32$^+$/CCR2$^+$ signals, increased CD206$^+$/CCR2$^+$ and ARG1$^+$/CCR2$^+$ signals in the perihematomal area at Day 3 (FIGS. 7C-E). These results suggest that modulation of M1/M2 polarization of macrophages may be involved in the neuroprotective effect of delayed Cav-1 inhibition.

The invention relates to the effect of Cav-1 inhibition by using a neutralizing antibody in experimental hemorrhagic stroke. The protective effect of anti-Cav-1 Ab treatment in ICH is supported by the following findings: 1) Anti-Cav-1 Ab treatment (icv injection) reduces ICH-induced brain injury. 2) Delayed anti-Cav-1 Ab treatment (i.v. injection) 3 hours after ICH reduces ICH-induced brain injury. 3) Anti-Cav-1 Ab treatment suppresses both ICH-induced inflammatory response, and thrombin-induced microglial inflammatory response. 4) Anti-Cav-1 antibody treatment (icv or i.v. injection) reduces microglial and infiltrated macrophage activation after ICH, modulates microglial and infiltrated macrophage polarization to reduce classically-activated M1-like (proinflammatory) microglia/macrophages and increases alternate-activated M2-like (anti-inflammatory) microglia/macrophages.

Anti-Cav-1 antibody via icv injection reduced microglial/macrophage activation and attenuated activation of p38 MAPK in mice subjected to ICH. Inhibition of Cav-1 improved long-term behavioral outcomes, attenuated brain edema, reduced brain tissue damage and neuronal death. Cav-1 inhibition attenuated thrombin-stimulated activation of P38 MAPK-AP-1/NF-κB signalings in microglial cultures. Anti-Cav-1 antibody treatment was still neuroprotective when using a more clinically relevant treatment time window via intravenous administration. Cav-1 may be a potential candidate to reduce post-hemorrhagic cerebral inflammatory responses mediated by microglia/macrophages.

Increased Cav-1 protein in Iba1$^+$ cells began at 6 hours post-ICH and Cav-1 Ab (icv injection) reduced cytokine expression as early as 6 hours, a time-point before recruitment of peripheral macrophages. Cav-1 Ab reduced thrombin-induced microglial activation in primary microglial cultures, suggesting that Cav-1 inhibition exert a direct effect on microglial activation. Delayed treatment of anti-Cav-1 Ab at 3 h post-ICH via i.v. reduced infiltration of CCR2$^+$ macrophages, suggesting that blood-derived macrophages are also a target for Cav-1-mediated inflammation. Besides suppressing the activation of classically activated M1 microglia/macrophages, anti-Cav-1 Ab induced microglia/macrophage polarization to alternately activated M2 Phenotype. The results imply an important role of Cav-1 inhibition in suppressing microglia/macrophage-mediated inflammatory responses and modulation on polarization of microglia/macrophage.

The role of Cav-1 in brain injury has been controversial. We found that inhibition of Cav-1 reduced ICH-induced brain injury and neuroinflammation, and attenuated thrombin-induced microglial activation in microglial cultures. Our results imply that Cav-1 is a crucial contributor to the deleterious effects of microglial/macrophage responses to ICH.

Figure 7:
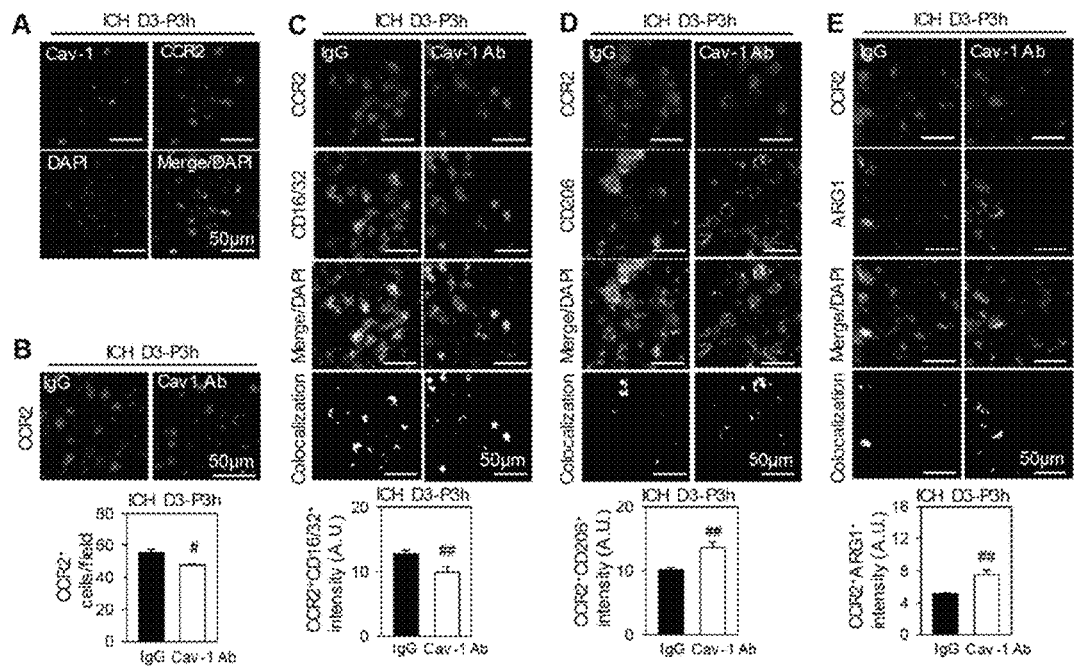
FIG. 7 shows delayed intravenous anti-Cav-1 treatment modulates M1/M2 polarization of infiltrated macrophages. Anti-Cav-1 Ab or control IgG (20 μg in 100 μl of saline) was intravenous injected through tail vein 3 hours after ICH. (A) Expression of Cav-1 in macrophages was detected by fluorescent colocalization of Cav-1 and CCR2 in control IgG-injected mice 3 days after ICH. (B) Infiltrated macrophages were quantified by CCR2 and DAPI staining 3 days after ICH (n=46). (C) Classical-activated (M1-like) macrophages were detected by fluorescent colocalization of $CCR2^+/CD16/32^+$ cells 3 days after ICH (n=6). (D, E) Alternative-activated (M2-like) macrophages were determined by fluorescent colocalization of (D) $CCR2^+/CD206^+$ and (E) $CCR2^+/ARG1^+$ cells 1 and 3 days after ICH (n=6). Sections were stained with DAPI to show all nuclei. Scale bar=50 μm. Values are mean±SEM. $^{\#}p<0.05$, $^{\#\#}p<0.01$ and $^{\#\#\#\#}p<0.001$ compared to ICH IgG group. (F) Model proposing how anti-Cav-1 Ab treatment modulates inflammatory response and its outcomes in brain protection after ICH.
Figure 7:
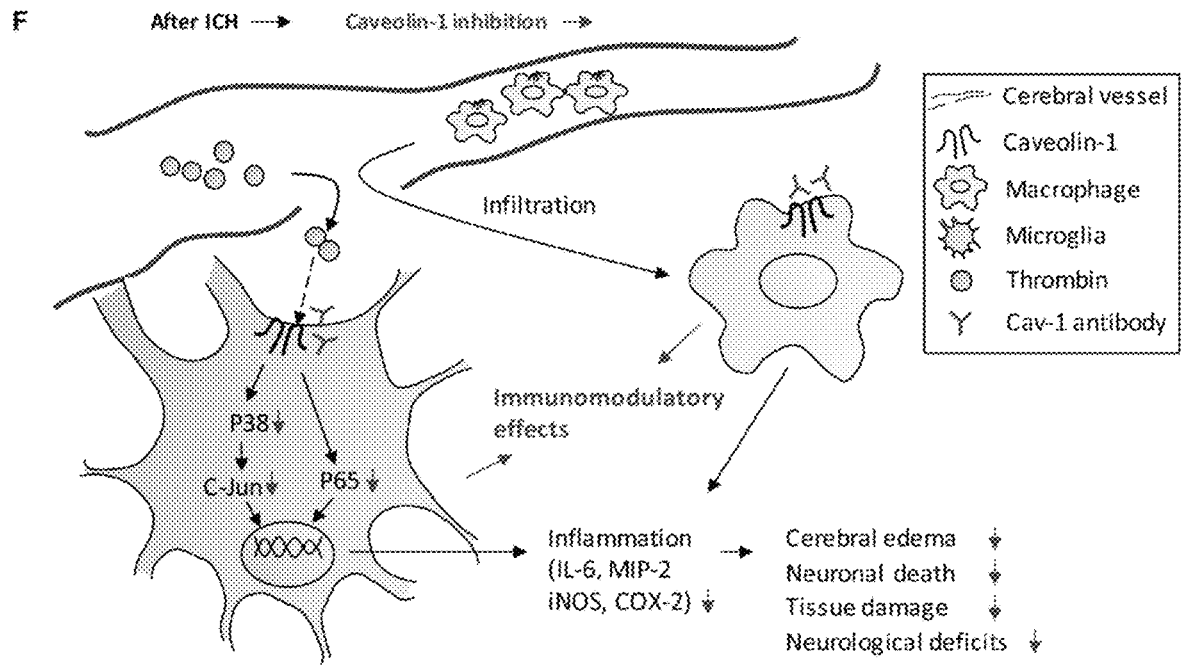

In conclusion, inhibition of Cav-1 improved neurological recovery, reduced brain tissue loss and brain edema, and limited neurodegeneration after ICH (FIG. 7). Inhibition of Cav-1 also suppressed ICH-induced proinflammatory microglia/macrophage activation. In cultured microglia, inhibition of Cav-1 reduced activation of P38 MAPK-AP and NF-κB signalings. Therefore, anti-Cav-1 antibody such as human monoclonal antibodies may have potential as a novel strategy for the treatment of ICH.

The foregoing description of the exemplary embodiments of the invention has been presented only for the purposes of illustration and description and is not intended to be exhaustive or to limit the invention to the precise forms disclosed. Many modifications and variations are possible in light of the above teaching. All references cited and discussed in this specification are incorporated herein by reference in their entireties and to the same extent as if each reference was individually incorporated by reference.

What is claimed is:

1. A method for treating intracerebral hemorrhage and/or a hemorrhagic stroke in a subject in need thereof, consisting of:
   administering via intravenous injection to the subject in need thereof a composition comprising:
   (a) a therapeutically effective amount of an antibody, the antibody consisting of a polyclonal caveolin-1 antibody; and
   (b) a pharmaceutically acceptable carrier,
   to treat the intracerebral hemorrhage and/or the hemorrhagic stroke in the subject in need thereof.

2. The method of claim 1, wherein the administering step is performed within 2 hours before occurrence of the intracerebral hemorrhage and/or the hemorrhagic stroke.

3. The method of claim 1, wherein the administering step is performed no later than 6 hours after occurrence of the intracerebral hemorrhage and/or the hemorrhagic stroke.

4. The method of claim 1, wherein the administering step is performed no later than 5 hours after occurrence of the intracerebral hemorrhage and/or the hemorrhagic stroke.

5. The method of claim 1, wherein the administering step is performed within 3 hours after occurrence of the intracerebral hemorrhage and/or the hemorrhagic stroke.

6. The method of claim 1, wherein the polyclonal caveolin-1 antibody is raised against human caveolin-1.

7. The method of claim 1, wherein the polyclonal caveolin-1 antibody is raised against an epitope at the N-terminus of human caveolin-1.

8. The method of claim 1, wherein the administering step is performed within 1 hour before occurrence of the intracerebral hemorrhage and/or the hemorrhagic stroke.

9. A method for improving behavioral outcomes or functional recovery in a subject with a hemorrhagic stroke, consisting of:
   administering via intravenous injection to the subject with the hemorrhagic stroke a composition comprising:
   (a) a therapeutically effective amount of an antibody, the antibody consisting of a polyclonal caveolin-1 antibody; and
   (b) a pharmaceutically acceptable carrier,
   to improve the behavioral outcomes or functional recovery in the subject with the hemorrhagic stroke.

10. The method of claim 9, wherein the behavioral outcomes are at least one selected from the group consisting of a neurological behavioral outcome and an asymmetric motor behavioral outcome.

11. The method of claim 9, wherein the behavioral outcomes or functional recovery is at least one selected from the group consisting of modified neurological severity score (mNSS) and elevated body swing test (EBST) ratio.

12. A method for reducing macrophage and neutrophil infiltration in a perihematomal area and/or suppressing microglia/macrophage-mediated inflammatory responses after intracerebral hemorrhage in a subject in need thereof, consisting of:
   administering vi intravenous injection to the subject in need thereof a composition comprising:
   (a) a therapeutically effective amount of an antibody, the antibody consisting of a polyclonal caveolin-1 antibody; and
   (b) a pharmaceutically acceptable carrier,
   to reduce the macrophage and neutrophil infiltration in the perihematomal area and/or suppress the microglia/macrophage-mediated inflammatory responses after the intracerebral hemorrhage in the subject in need thereof.

13. The method of claim 12, wherein the administering step is performed within 1-24 hours window of the occurrence of the hemorrhagic stroke.

14. The method of claim 12, wherein the administering step is performed within 3-24 hours window of the occurrence of the hemorrhagic stroke.

* * * * *